(12) United States Patent
Takahashi et al.

(10) Patent No.: US 7,189,976 B2
(45) Date of Patent: Mar. 13, 2007

(54) METHOD FOR GENERATING HIGH-SPEED PARTICLE AND SYSTEM FOR GENERATING HIGH-SPEED PARTICLE

(75) Inventors: Hironori Takahashi, Hamamatsu (JP); Takashi Inoue, Hamamatsu (JP); Shinji Ohsuka, Hamamatsu (JP); Yutaka Tsuchiya, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 130 days.

(21) Appl. No.: 10/533,441

(22) PCT Filed: Dec. 19, 2003

(86) PCT No.: PCT/JP03/16402

§ 371 (c)(1),
(2), (4) Date: May 2, 2005

(87) PCT Pub. No.: WO2004/057625

PCT Pub. Date: Jul. 8, 2004

(65) Prior Publication Data

US 2006/0013269 A1     Jan. 19, 2006

(30) Foreign Application Priority Data

Dec. 20, 2002   (JP)   .............................. 2002-370441

(51) Int. Cl.
*H01S 3/10*   (2006.01)
*G21K 1/00*   (2006.01)
*H05H 1/24*   (2006.01)

(52) U.S. Cl. ................................. 250/423 R; 250/424

(58) Field of Classification Search ............. 250/423 R
See application file for complete search history.

(56) References Cited

U.S. PATENT DOCUMENTS

| 5,420,436 | A  | * | 5/1995 | Seya et al. ................ 250/492.1 |
| 6,724,004 | B2 | * | 4/2004 | Yashiro .................... 250/504 R |
| 6,767,743 | B2 | * | 7/2004 | Takayama et al. ........... 435/459 |
| 6,909,764 | B2 | * | 6/2005 | Maksimchuk et al. ....... 376/190 |

(Continued)

OTHER PUBLICATIONS

Backus et al., "High Power Ultrafast Lasers", Rev. Sci. Instruments 69 (3), 1998, pp. 1207-1223.*

(Continued)

*Primary Examiner*—Nikita Wells
*Assistant Examiner*—Bernard Souw
(74) *Attorney, Agent, or Firm*—Drinker Biddle & Reath LLP

(57) ABSTRACT

The present invention relates to a high-speed particle generating method and so on for generating high-speed particles from a high-speed particle generating target by condensing a pulsed laser beam to a micro-spot on the surface of a high-speed particle generating target. The high-speed particle generating method is a method that generates high-speed particles by condensing a pulsed laser beam generated from a pulsed laser beam generator through an irradiation optical system at a predetermined condensing point, and irradiating the pulsed laser beam to the high-speed particle generating target that is set at the predetermined condensing point, the method including a first step of preparing a reference data, a second step of measuring the wave front of the pulsed laser beam, and a third step of compensating the wave front of the pulsed laser beam based on the reference data.

4 Claims, 12 Drawing Sheets

U.S. PATENT DOCUMENTS

2002/0172317 A1* 11/2002 Maksimchuk et al. ...... 376/190
2003/0080302 A1*  5/2003 Yashiro ................. 250/504 R
2003/0104627 A1*  6/2003 Takayama et al. ......... 435/459

OTHER PUBLICATIONS

Group for High Energy Physics, Institute of Physics, Chinese Academy of Sciences 2003, <http://highfield.iphy.ac.cn/L05/Research.html>.*

Akaoka et al., "Closed loop wavefront correction of Ti: sapphire Chirped Pulse Amplification laser beam," SPIE, Jan. 1998, vol. 3265, pp. 219-225.

Spencer et al., "Laser generation of proton beams for the production of short-lived positron—emitting radiosotopes," Nuclear Instruments and Methods in Physics Research B 183 (2001), pp. 459-458.

Albert et al., "Generation of relativistic intensity pulses at a kilohertz repetition rate," Optics Letters, vol. 25, No. 15, Aug. 1, 2000, pp. 1125-1127.

Central Laser Facility Annual Report 2000/2001.

* cited by examiner

METHOD FOR GENERATING HIGH-SPEED PARTICLE AND SYSTEM FOR GENERATING HIGH-SPEED PARTICLE

TECHNICAL FIELD

The present invention relates to a high-speed particle generating method and a high-speed particle generating apparatus that generate high-speed particles from a high-speed particle generating target by irradiating a pulsed laser beam to a high-speed particle generating target.

BACKGROUND ART

In a high-speed particle generating apparatus for generating high-speed particles by irradiating a pulsed laser beam to a high-speed particle generating target, it is necessary to condense a laser beam to a micro-spot on the target surface in order to generate the high-speed particles efficiently. However, there are many cases that in a high-intensity laser beam, the laser beam itself to be outputted has been already distorted. In addition to the beam diameter expanding due to distortion of the wave front generated during the propagation, the wave front also may be distorted due to thermal deformation of the optical system. As a result, there are some cases that the spot diameter of the laser beam at a condensing point (condensing position) is not reduced.

Conventionally, in order to enhance an optical intensity by converging a laser beam to a micro-spot, a wave front compensation control adjusting a wave front of the laser beam is conducted. For example, in Katsuaki Akaoka et al., "Closed loop wavefront correction of Ti: sapphire Chirped Pulse Amplification laser beam," SPIE, Vol. 3265, 29–30, Jan. 1998, p. 219–225, a technique for compensating for the wave front of a laser beam is disclosed to set a He—Ne laser as a reference light source in an optical path of a high-intensity laser, measure the wave front outputted from the reference light source at a wave front sensor, and stores its measurement results as a reference wave front, so that the wave front of the laser beam from a titanium sapphire laser is conformed with the reference wave front.

DISCLOSURE OF THE INVENTION

After studying the foregoing prior art, the inventors and others find out the following problems. Namely, in the wave front compensating method described in the above reference, the spot diameter of the laser beam in the condensing position (typically condensing at a focal point of optical systems) cannot be reduced sufficiently; consequently, a sufficient optical intensity cannot be obtained. Therefore, there is a problem that in the conventional wave front compensating method, high-speed particles cannot be generated efficiently.

The present invention is made to overcome the aforementioned problems, and it is an object to provide a high-speed particle generating method and a high-speed particle generating apparatus having an construction for generating high-speed particles from a high-speed particle generating target by condensing a pulsed laser beam at a micro-spot on the surface of the high-speed particle generating target.

A high-speed particle generating method according to the present invention condenses a pulsed laser beam generated from a pulsed laser beam generator at a predetermined condensing point through an irradiation optical system, and irradiates the condensed pulsed laser beam to a high-speed particle generating target that is set at the predetermined condensing point, thereby generating high-speed particles from the set high-speed particle generating target. More specifically, the high-speed particle generating method comprises: a first step of recording information concerning a reference wave front; a second step of measuring the wave front of the pulsed laser beam; and a third step of compensating the wave front of the measured pulsed laser beam based on the information concerning the recorded reference wave front. Additionally, the first step irradiates a reference light from the predetermined condensing point, measures the wave front of that reference light by a wave front measuring device, and stores the measured wave front as a reference wave front. The second step measures the wave front of the pulsed laser beam generated from the wave front measuring device and passing through the predetermined condensing point by the wave front measuring device. The third step compensates the wave front of the pulsed laser beam generated from the pulsed laser beam generator based on the reference wave front recorded at the first step.

In accordance with the aforementioned high-speed particle generating method (high-speed particle generating method according to the present invention), the wave front of the reference light generated from the predetermined condensing point to be set by the, high-speed particle generating target is measured and stored as reference wave guide information, while the wave front of the pulsed laser beam generated from the pulsed laser beam generator and passing through the above predetermined condensing point is measured, and then the wave front of the pulsed laser beam generated from the pulsed laser beam generator is compensated based on the reference wave front. In such a way, the pulsed laser beam is condensed to the micro-spot at the predetermined condensing point, and consequently irradiated to the high-speed particle generating target to be set at the predetermined condensing point, which enables to generate high-speed particles from the high-speed particle generating target efficiently.

On the other hand, a high-speed particle generating apparatus according to the present invention comprises: a target unit, a pulsed laser beam generator, a wave front compensating unit, and an irradiation optical system. More specifically, the target unit holds a high-speed particle generating target at a predetermined position. In addition, the high-speed particle generating target generates high-speed particles based on laser plasma generated due to irradiation of a pulsed laser beam. The pulsed laser beam generator generates a pulsed laser beam. The wave front compensating unit compensates the wave front of the pulsed laser beam. The irradiation optical system condenses at a predetermined condensing point the pulsed laser beam to be wave-front-compensated by the wave front compensating unit for the high-speed particle generating target. In particular, in the high-speed particle generating apparatus according to the present invention, it is preferable that the wave front compensating unit comprises: a deformable optical system, a reference light source, a wave front measuring device, a recording (storing) unit, a deformable optical system control unit, and a displacement mechanism. In the deformable optical system, the optical operation unit of optical elements for reflecting or deflecting the pulsed laser beam is deformably constituted. The reference light source generates a reference light from the predetermined condensing point. The wave front measuring device measures the wave front of the reference light and the wave front of the pulsed laser beam passing through the predetermined condensing point, respectively. The recording unit stores the wave front of the reference light measured by the wave front measuring device as a reference wave front. The deformable optical system control unit compensates the wave front of the pulsed laser beam in such a manner that the optical operation unit is deformed based on the reference wave front and the wave front of the pulsed laser beam measured by the wave front measuring device. The displacement mechanism displaces the reference light source so that the irradiation position of the reference light is conformed at the predetermined condensing point, or displaces the target unit so that the high-speed particle generating target is conformed with a plane including the predetermined condensing point.

In accordance with the high-speed particle generating apparatus having the aforementioned construction (high-speed particle generating apparatus according to the present invention), the wave front of the reference light generated by the reference light source from the predetermined condensing point (position to be set by the high-speed particle generating target) is stored by the storing unit as the reference wave front. Then, the wave front of the pulsed laser beam passing through the condensing point and generated from the pulsed laser beam generator is also measured. The wave front of the pulsed laser beam is compensated in such a manner that the optical operation unit is deformably controlled based on the wave front of the pulsed laser beam and the reference wave front stored in the storing unit. Therefore, when the displacement mechanism displaces the target unit so that the high-speed particle generating target is positioned on the plane including the condensing point, the condensed pulsed laser beam can be, irradiated to the micro-spot, thereby generating high-speed particles from the high-speed particle generating target.

Further, in the high-speed particle generating apparatus according to the present invention, the wave front compensating unit may comprise: a deformable optical system, a reference light generating unit, a wave front measuring device, a storing unit, a deformable optical system control unit, and a displacement mechanism. In the deformable optical system, the optical operation unit of the optical element for reflecting or deflecting the pulsed laser beam is deformably constituted. The reference light generating unit has a pinhole that generates the reference light from the predetermined condensing point by passing through the pulsed laser beam. The wave front measuring device measures the wave front of the reference light and the wave front of the pulsed laser beam passing through the predetermined condensing point, respectively. The storing unit stores the wave front of the reference light measured by the wave front measuring device as the reference wave front. The deformable optical system control unit compensates the wave front of the pulsed laser beam in such a manner that the optical operation unit is deformed based on the reference wave front and the wave front of the pulsed laser beam measured by the wave front measuring device. Then, the displacement mechanism displaces the reference light generating unit and the high-speed particle generating target, respectively, on the plane including the predetermined condensing point.

In accordance with the high-speed particle generating apparatus having the aforementioned construction, the wave front of the reference light generated by the reference light generating unit from the predetermined condensing point (position to be set by the high-speed particle generating target) is stored by the storing unit as the reference wave front. Then, since the wave front of the pulsed laser beam passing through the condensing point and generated from the pulsed laser generator is also measured, when the optical operation unit of the optical element is deformably controlled based on the wave front of the pulsed laser beam and the reference wave front stored in the storing unit, the wave front of the pulsed laser beam is compensated. Therefore, when the displacement mechanism displaces the target unit so that the high-speed particle generating target is positioned on the plane including the condensing point, the condensed pulsed laser beam can be irradiated to the micro-spot, thereby generating high-speed particles from the high-speed particle generating target.

In addition, in the high-speed particle generating apparatus according to the present invention, preferably, the high-speed particle generating target is formed on the surface of a membrane target member, an opening and a pinhole passing the pulsed laser beam is formed in the target member, and the wave front of the pulsed laser beam passing through the opening is measured by the wave front measuring device. In this case, since the opening and pinhole passing through the pulsed laser beam is formed by the same target member as that of the high-speed particle generating target, it becomes possible to measure the wave front of the reference light and the wave front of the pulsed laser beam, respectively, and compensate the wave front of the pulsed laser beam with high positional precision.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BEST MODE OF CARRYING OUT THE INVENTION

In the following, embodiments of a high-speed particle generating method and a high-speed particle generating apparatus according to the present invention will be explained in detail with reference to FIGS. 1–12. In the explanation of the drawings, the same elements will be denoted by the same reference symbols and these redundant descriptions will be omitted.

First Embodiment

Figure 1:
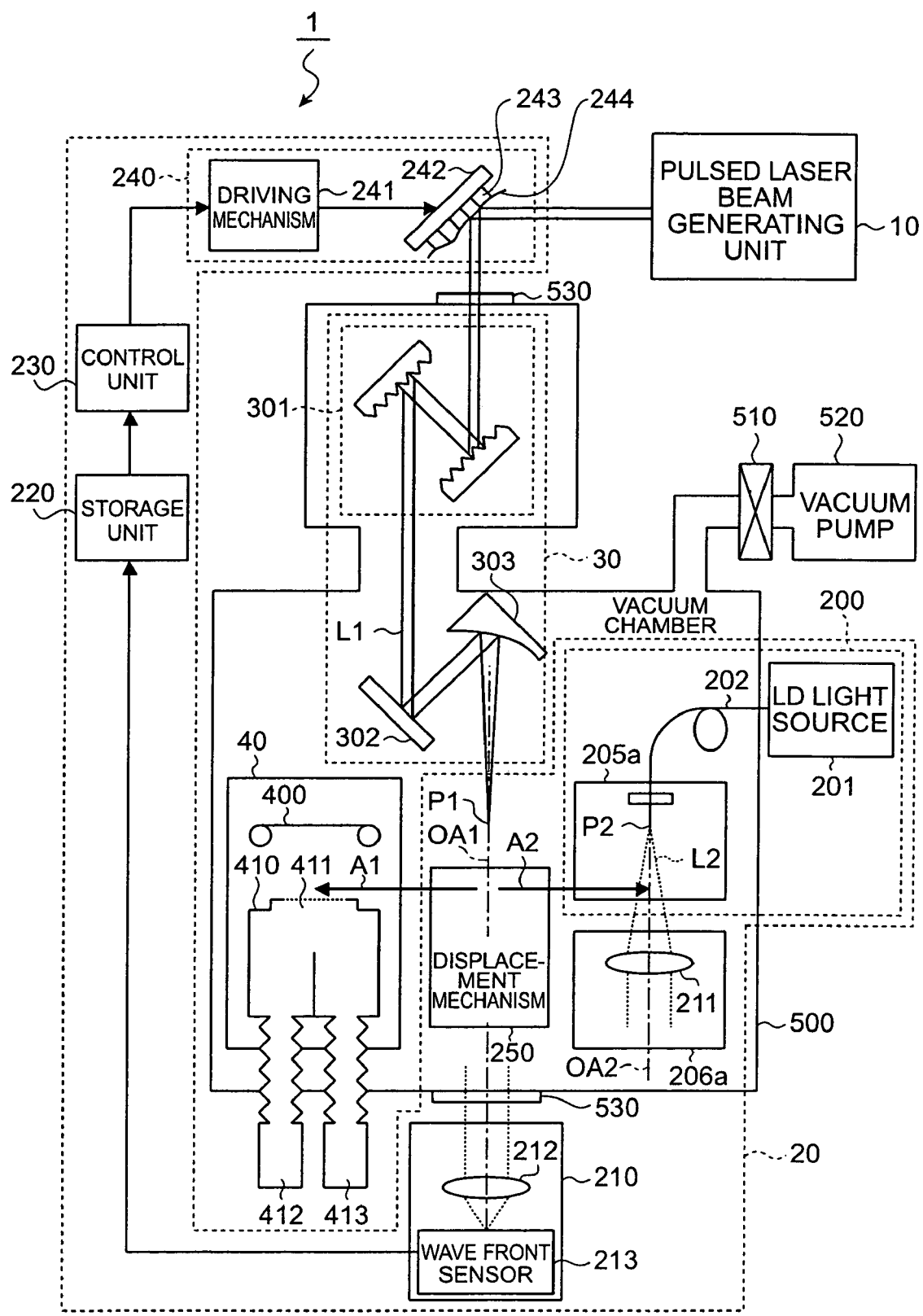
FIG. 1 is a view showing a construction of a first embodiment of a high-speed particle generating apparatus according to the present invention.

FIG. 1 is a view showing a construction of a first embodiment of a high-speed particle generating apparatus according to the present invention. As shown in FIG. 1, a high-speed particle generating apparatus 1 according to the first embodiment comprises: a pulsed laser beam generating unit 10; a wave front compensating unit 20; an irradiation optical system 30; and a target unit 40. In addition, the pulsed laser beam generating unit 10 generates a high peak-power pulsed laser beam L1. The wave front compensating unit 20 compensates the wave front of the pulsed laser beam L1. Then, the target unit 40 includes a component for generating high-speed particles by irradiation of the pulsed laser beam L1.

For example, a titanium sapphire laser for outputting the high peak-power pulsed laser beam L1 having a wavelength of 800 nm, a pulse width of 130 fs, and a maximum energy of 200 mJ, and so on is suitable for the pulsed laser beam generating unit 10. In addition, the pulsed laser beam generating unit 10 includes a regenerative amplifier and a multipass amplifier.

The wave front compensating unit 20 compensates the wave front of the pulsed laser beam L1 outputted from the pulsed laser beam generating unit 10, and outputs the wave front compensated pulsed laser beam to the irradiation optical system 30.

The irradiation optical system 30 comprises: a pair of gratings for pulse-compressing the pulsed laser beam L1 entering from the wave front compensating unit 20; a mirror reflector 302 for reflecting the pulse-compressed pulsed laser beam L1 and outputting the resultant to an off-axis parabolic mirror 303; and the off-axis parabolic mirror 303 for condensing the pulsed laser beam L1 reflected by the mirror reflector 302 to be entered, and for irradiating the resultant to the target unit 40.

The target unit 40 includes a component that generates high-speed particles such as electrons and ions of high-energy, a radioactive isotope of high energy, and so on, and includes specifically a high-speed particle generating target 400 and an isotope generating unit 410. The pulsed laser beam L1 is irradiated to the target surface of the high-speed generating target 400 in a condensed state to produce laser plasma, and the high-speed particles such as electrons and ions of high-energy are generated by the laser plasma. However, the detail of the high-speed particles generating target 400 will be described later.

The isotope generating unit 410 comprises a reaction unit 411, a material feeding unit 412 and a product storage unit 413. The material feeding unit 412 feeds a radioactive isotope generating material to the reaction unit 411. The reaction unit 411 triggers a nuclear reaction in such a manner that high-speed particles generated from the high-particle generating target 400 are further collided with the radioactive generating material fed from the material feeding unit 412, thereby resulting in a variety of radioactive isotopes. The product storage unit 412 recovers and stores the radioactive isotope obtained from the reaction unit 411.

It is noted that the target unit 40 can reciprocate a linear motion in the directions of arrow A1 and arrow A2 that are perpendicular to the optical axis OA1 of the pulsed laser beam L1 by means of a displacement mechanism 250 in a state holding the high-speed particle generating target 400.

The wave front compensating unit 20 compensating the wave front of the pulsed laser beam L1 comprises a deformable optical system 240, a reference light source 200, a collimator unit 206a, a wave front measuring unit 210, a storage unit 220, a control unit (deformable optical system control unit) 230, and the displacement mechanism 250. The deformable optical system 240 is constituted such that a reflecting surface 244 of a deformable mirror 242 for reflecting the pulsed laser beam L1 is deformable. The reference light source 200 generates a reference light L2. The collimator unit 206a makes each of the reference light L2 and pulsed laser beam L1 into parallel pencil of rays. The wave front measuring unit 210 conducts measurements of the respective wave fronts of the reference light L2 and pulsed laser beam L1. The storage (recording) unit 220 stores the wave front of the reference light L2. The control unit 230 compensates the wave front of the pulsed laser beam L1 based on the wave front of the wave front of the reference light L2 and the wave front of the pulsed laser beam L1. The displacement mechanism 250 displaces the reference light source 200, collimator unit 206a, and target unit 40 independently.

The reference light source 200 is an optical device for outputting the reference light L2, and comprises a LD (laser diode) light source 201, a single-mode optical fiber 202, and a reference light outputting unit 205a, The LD light source 201 generates a laser beam (reference light L2) having the substantially same wavelength (780–830 nm) as that of the pulsed laser beam L1. The single-mode optical fiber 202 is an optical waveguide for guiding the reference light L2 emitted from the LD light source 201 to an emission point P2. The reference light outputting unit 205a is a component for displacing the emission point P2 of the reference light L2 guided by the optical fiber 202, and allows to reciprocate a linear motion.

The collimator unit 206a includes a collimator lens 211. The collimator lens 211 is an optical component that makes each of the reference light L2 and pulsed laser beam L1 into parallel pencil of rays. Additionally, the collimator unit 206a is constructed to be able to reciprocate a linear motion in the directions of arrow A1 and arrow A2 by the displacement mechanism 250.

The wave front measuring unit 210 comprises an imaging lens 212 and a wave front sensor 213 so as to measure the respective wave fronts of the reference light L1 outputted from the reference light source 200 and the pulsed laser beam L1. The imaging lens 212 is an optical component for imaging the reference light L2 incident from the collimator unit 206a and the pulsed laser beam L1 independently on the wave front sensor 213. In addition, the wave front sensor 213 is a device for measuring the respective wave fronts of the reference light L2 and pulsed laser beam L1, and is adapted by, for example, a Shack-Hartmann sensor and so on. The detail of the wave front sensor 213 will be described later.

In addition, the wave front measuring unit 210 measures the wave front of the reference light L2 in a state that the reference light outputting unit 205a and collimator 206a each are arranged on the optical path of the pulsed laser beam L1 by the displacement mechanism 250, and only the collimator 206a measures the wave front of the pulsed laser beam L1 in a state arranged on the optical path of the pulsed laser beam L1.

The storage unit 220 is a device for storing the wave front of the reference light L2 measured by the wave front sensor 213 as a reference wave front, and is adapted by, for example, a hard disk and an optical disk, and so on.

Based on the wave front of the pulsed laser beam L1 measured by the wave front measuring unit 210 and the reference wave front stored in the storage unit 220, the control unit 230 compensates the wave front of the pulsed laser beam L1 by deforming the shape of a reflecting surface 244 of a deformable mirror 242 so that the wave front of the pulsed laser beam L1 is conformed with the reference wave front. For instance, computers and so on are suitable for the control unit 230.

A deformable variable optical system 240 comprises a driving unit 241 and the deformable mirror 242 so that the shape of the mirror reflector 244 for reflecting the pulsed laser beam L1 is deformably constituted. The deformable mirror 242 includes an actuator 243 arrayed two-dimensionally at the lower portion of the thin mirror reflector 244, and the shape of the mirror reflector 244 is deformed when the actuator 243 is driven by a driving mechanism 241. In addition, the driving mechanism 241 drives the actuator 243 in accordance with the control data from the control unit 230. For instance, a Bimorph-type deformable mirror is suitable for the deformable mirror 242.

A displacement mechanism 250 makes the reference light outputting unit 205a, collimator 206a, and target unit 40 reciprocate a linear motion in the directions of arrow A1 and arrow A2 independently.

In addition, the irradiation optical system 30, high-speed particle generating unit 40, optical fiber 202, reference light outputting unit 205a, collimator unit 206a and displacement mechanism 250 are housed in a stainless-made or the like vacuum chamber 500. A gate value 510 and a vacuum pump 520 are connected to the vacuum chamber 500, and the inside of the vacuum chamber 500 is maintained in a vacuum state (approximately $1 \times 10^{-3}$ Pa) by the vacuum pump 520. Further, the vacuum chamber 500 has a view port made of quartz coated by a anti-reflection film to transmit the laser beam.

The operation of the high-speed particle generating apparatus 1 according to the first embodiment will next be explained with reference to FIG. 2, and a high-speed particle generating method will be also explained.

Figure 3:
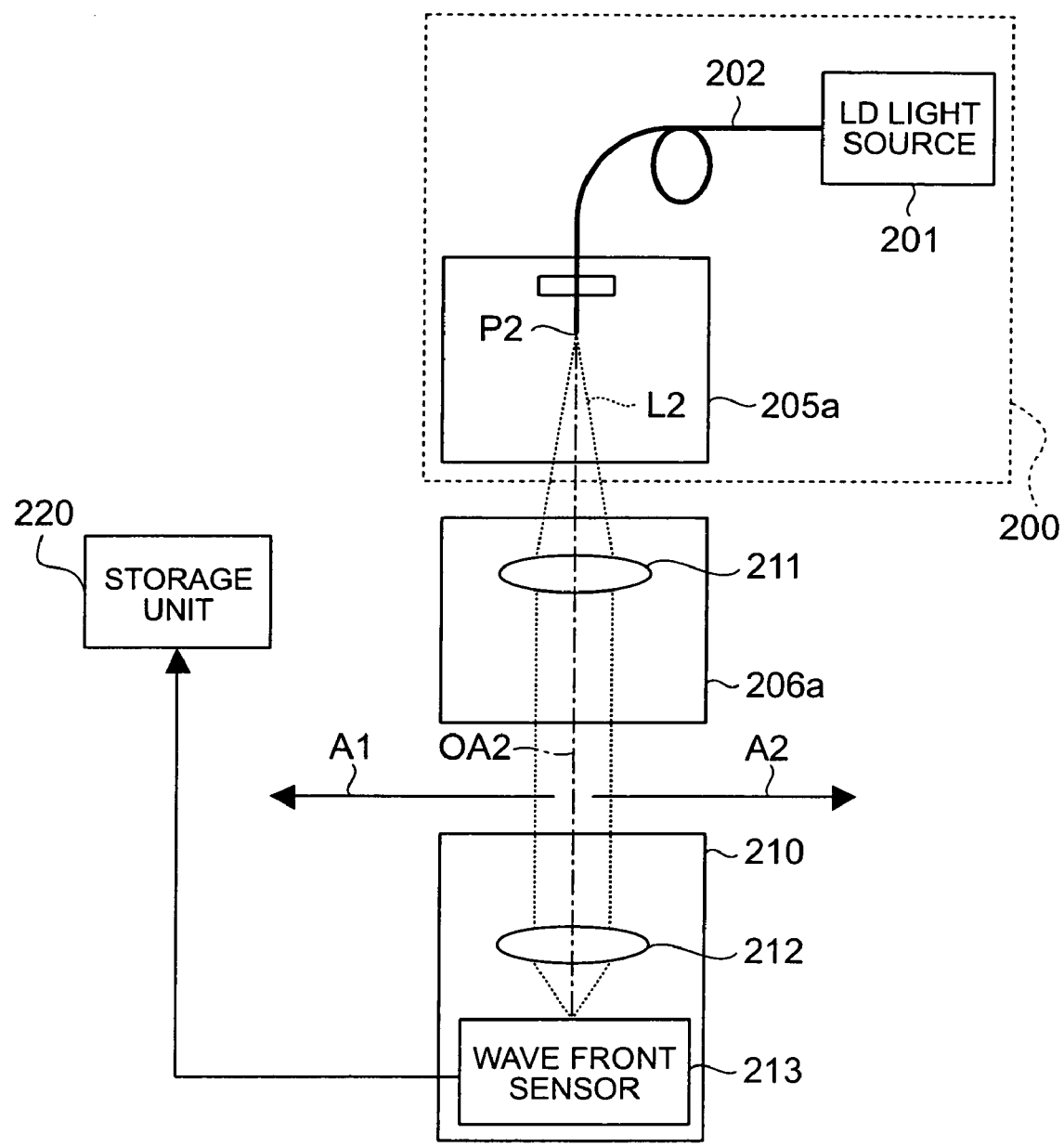
FIG. 3 is a view showing an arrangement in a reference wave front measuring process.

At step S100, as shown in FIG. 3, the reference light outputting unit 205a and collimator unit 206a each are displaced in the direction of arrow Al by the displacement mechanism 250 so that the optical axis OA2 of the reference light L2 is conformed with the optical axis OA1 of the pulsed laser beam L1. At this time, the emitting point P2 of the reference light L2 is arranged at the position to be conformed with the condensing point P1 of the pulsed laser beam L1.

Then, the reference light L2 having the substantially same wavelength as that of the pulsed laser beam L1 is emitted from the LD light source 201, and guided from the optical fiber 202 to the emitting point P2 to be outputted. The reference light L2 outputted from the optical fiber 202 is turned to a collimated beam by the collimator lens 211, imaged on the wave front sensor by the imaging lens 212, and then the corresponding wave front is measured by the wave front sensor 213.

Figure 4:
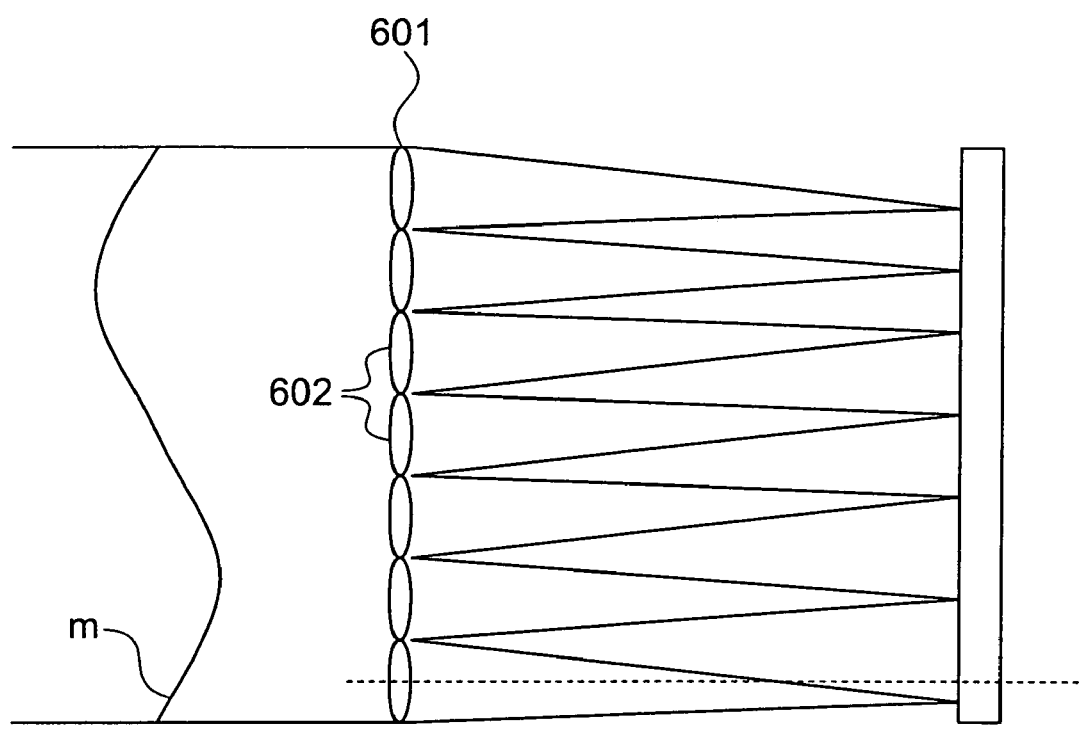
FIG. 4 is a view for explaining a basic principle of Shack-Hartmann methods.

The wave front sensor 213 will now be explained. As shown in FIG. 4, for instance, in the wave front sensor 213 applying a Shack-Hartmann method, a lens array 601 is arranged at the pupil position of the optical system, and images produced from separate lenses 602 are stored in a CCD camera, and the slope of the wave front is measured based on the positional change of independent spots. In this case, the positional change of the focal spot depends on the local slop of an incident wave front m. Thus, it becomes possible to measure the slope of the incident wave front m when all the spot positions are measured.

Figure 2:
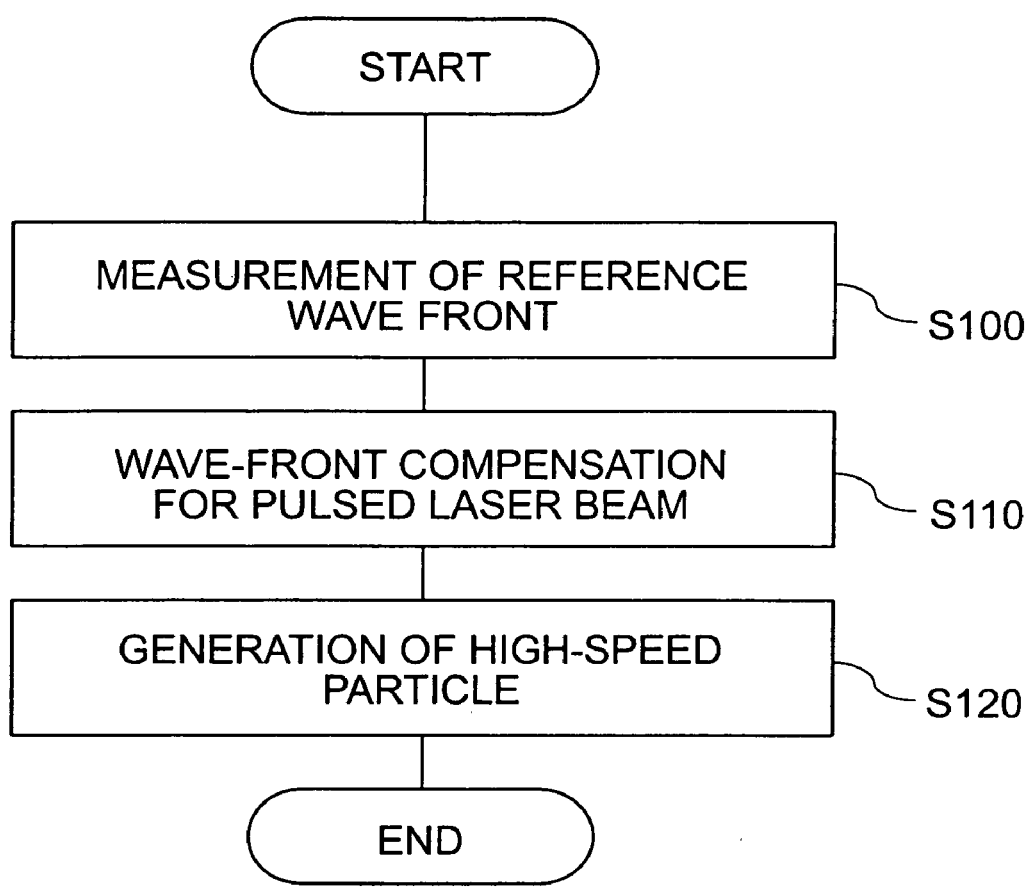
FIG. 2 is a flow chart showing the whole process of a high-speed particle generating method according to the present invention.

Continuing the explanation of the whole process coming back to FIG. 2, the wave front of the reference light L2 measured by the wave front sensor 213 is stored as a reference wave front by the storage unit 220. Incidentally, the measurement data of the reference wave front is not changed when the respective positional relationships of the reference light source 200, collimator unit 206a and wave front measuring unit 210 are constant. Therefore, it is not necessary to carry out the measurement of the wave front of the reference light L2 for every generation of high-speed particles as long as the aforementioned positional relationships do not change.

Figure 5:
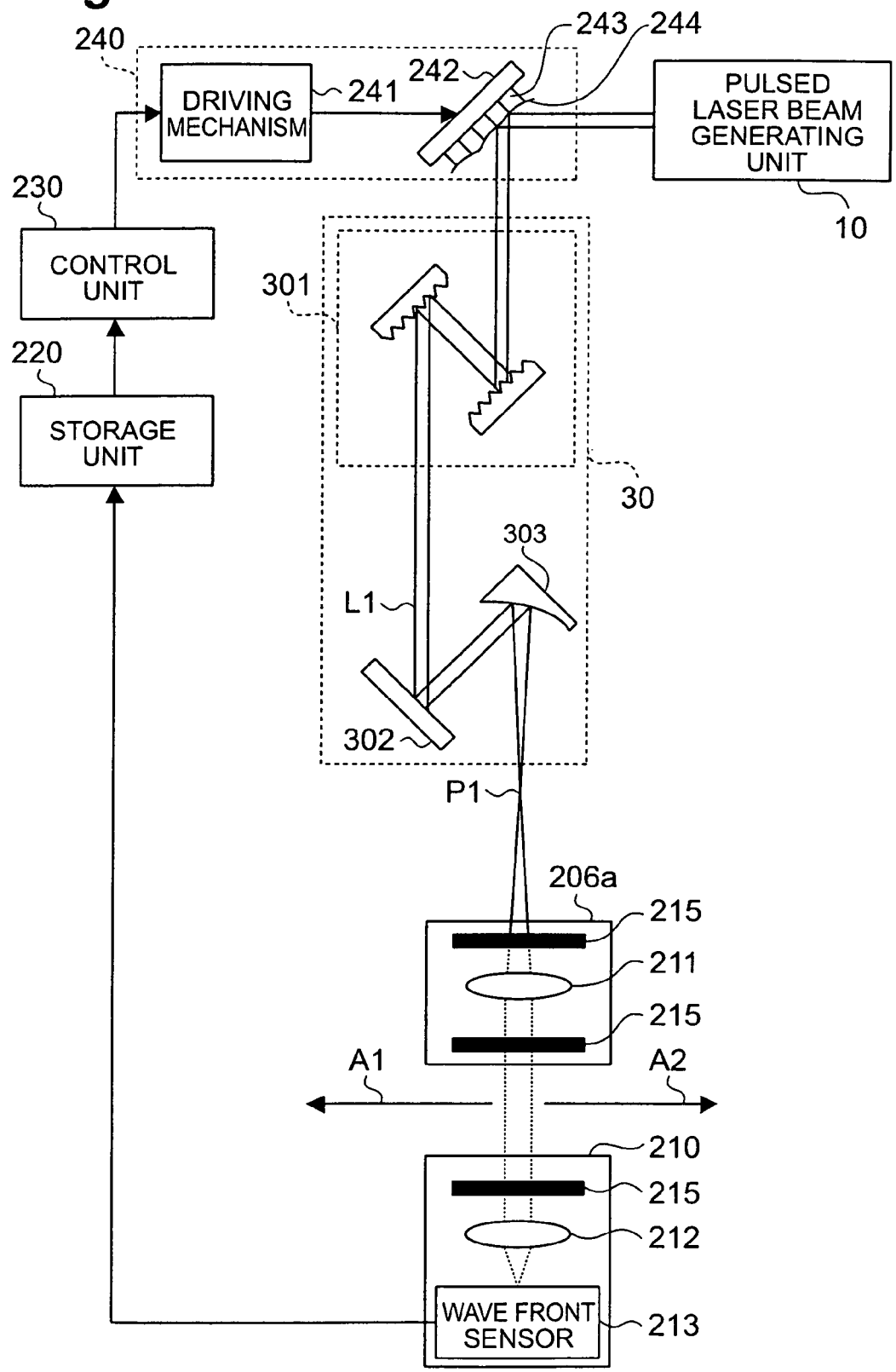
FIG. 5 is a view showing an arrangement in a wave front compensation process of pulsed laser beams.

Then, at step S110, the displacement mechanism 250 displaces the reference light outputting unit 205a in the direction of arrow A2, and thereby the reference light outputting unit 205a is removed from the optical path of the pulsed laser beam L1. On the other hand, as shown in FIG. 5, the collimator unit 206a is left on the optical path. Further, in order to prevent the breakage of the wave front sensor 2 13 by incidence of the pulsed laser beam L1, an ND (Neutral Density) filter (attenuation filter) 215 is additionally placed on the optical path of the pulsed laser beam L1.

Next, the pulsed laser beam L1 is outputted from the pulsed laser beam generating unit 10. The pulsed laser beam L1 is reflected by the deformable mirror 242, pulse-compressed by the pair of gratings 301, and then reflected by the mirror reflector 302, to be outputted to the off-axis parabolic mirror 303. The pulsed laser beam L1 incident on the off-axis parabolic mirror 303 is once condensed at the condensing point P1, and then the energy of the beam L1 is attenuated by the ND filter 215 and incident on the wave front sensor 213. Then, the wave front of the pulsed laser beam L1 is measured by the wave front sensor 213.

The measurement data on the wave front of the pulsed laser beam L1 measured by the wave front sensor 213 is outputted to the control unit 230 through the storage unit 220. Then, an operation is carried out by the control unit 230 so that the wave front of the pulsed laser beam L1 is conformed with the reference wave front stored in the storage unit 220 (computation of control data). Then, according to the control data, the actuator 243 attached to the deformable mirror 242 is driven by the driving unit 241, and the shape of the reflecting surface 244 of the deformable mirror 242 is deformed. Here, a Bimorph-type deformable mirror having the number of thirty one electrodes, an aperture diameter of 50 mm, and a stroke of 20 μm (peak barrel) was employed for the deformable mirror 242.

As described above, the wave front of the pulsed laser beam L1 is compensated so as to be conformed with the wave front (reference wave front) of the reference light L2.

Figure 6:
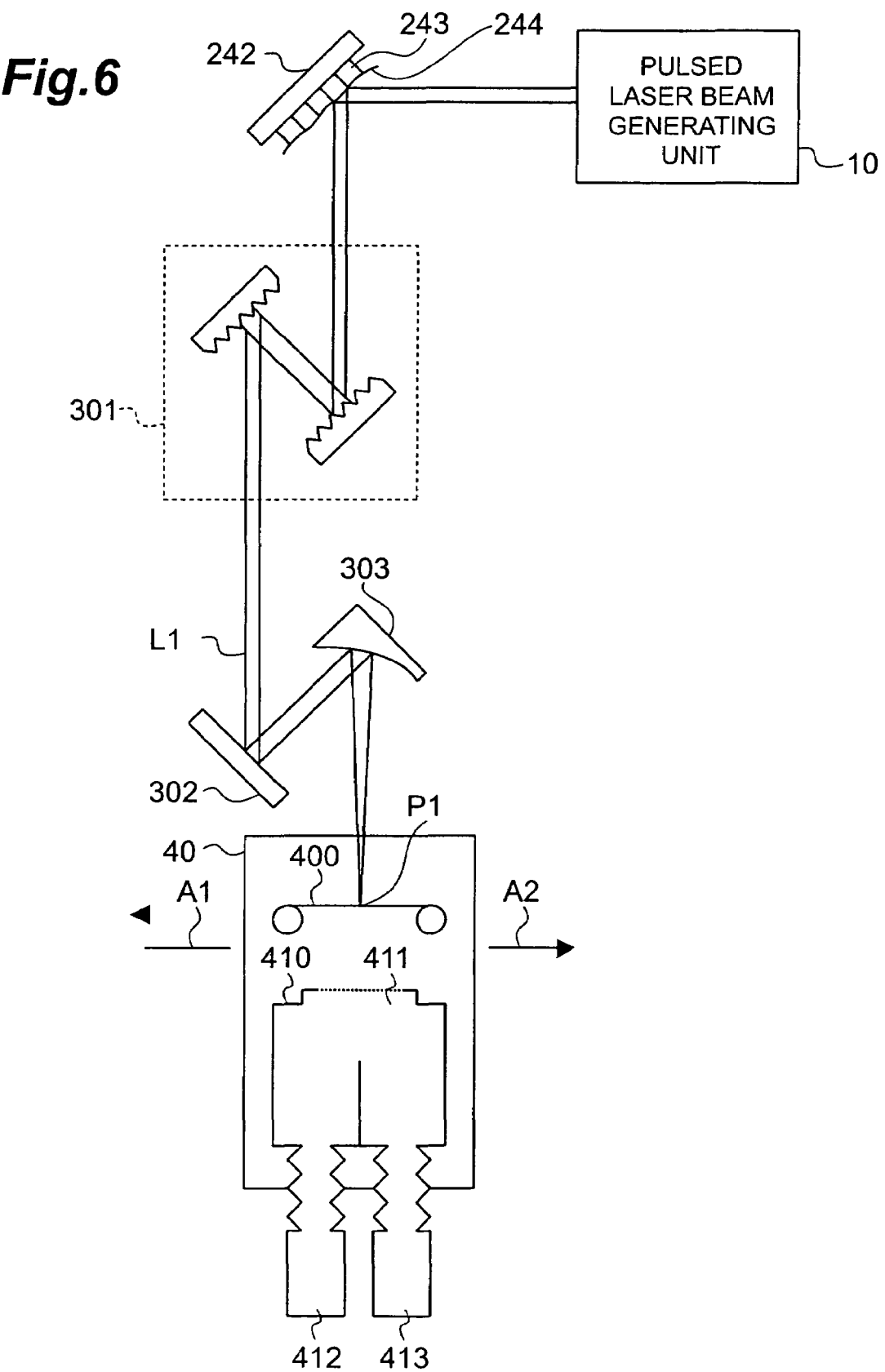
FIG. 6 is a view showing an arrangement in a high-speed particle generation process.

At step S120, the displacement mechanism 250 displaces the collimator unit 206a and ND filter. 215 in the direction of arrow A2, and thereby the collimator unit 206a and ND filter 215 is removed from the optical path of the pulsed laser beam L1. Then, as shown in FIG. 6, the displacement mechanism 250 displaces the target unit 40 in the direction of arrow A2, and thereby the target unit 40 is arranged on the optical path of the pulsed laser beam L1. At this time, since the high-speed particle generating target 400 is arranged on a plane including the condensing point P1, the condensing point P1 of the pulsed laser beam L1 may be positioned on the surface of the high-speed particle generating target 400.

Next, the high peak-power pulsed laser beam L1 is outputted from the pulsed laser beam generating unit 10. The pulsed laser beam L1 is incident on the deformable mirror 242, and that wave front is compensated by the deformable mirror 242. The pulsed laser beam L1 outputted from the deformable mirror 242 is pulse-compressed by the pair of gratings 301, and then reflected by the mirror reflector 302 and outputted to the off-axis parabolic mirror 303. Then, the resultant is condensed by the off-axis parabolic mirror 303 and irradiated to the high-speed particle generating target 400. It is noted that since the wave front of the high-intensity laser L1 is compensated to conform with the reference wave front at the condensing point P1 by the deformable mirror 242, it is condensed to a micro-spot (diameter: approximately 10 μm) on the surface of the high-speed particle target 400.

Then, in the high-speed particle target 400 irradiated by the condensed pulsed laser beam L1, laser plasma is produced on the surface of the target, and high-speed particles such as high-energy electrons or ions are generated from the laser plasma.

The generation mechanism of the high-speed particles will now be explained. When the high peak-power pulsed laser beam L1 is condensed on the high-speed particle generating target 400, laser plasma is generated on the target surface. The pulsed laser beam L1 forms a plasma wave on propagating in the plasma, and electrons are accelerated by the plasma wave. In addition, electrons are accelerated in the propagating direction of the pulsed laser beam L1 and the reverse direction thereof by a strong ponderamotive force. At this time, when the high-speed particle generating target 400 is sufficiently thin, accelerated electrons are discharged from the target. In addition, ions are drawn out due to a static electric field formed by a high-energy component of electrons, and high-energy ions are discharged in a beam shape in the propagating direction of the pulsed laser beam L1 and its reverse direction.

Returning to the explanation of the whole process, high-speed particles such as high-energy ions generated from the high-speed particle generating target 400 fly to the reaction unit 411, and collide with a radioactive isotope generating material fed from the material feeding unit 412 in the reaction unit 411, thereby triggering a nuclear reaction. As a result, a variety of radioactive isotopes can be obtained. Incidentally, the radioactive isotope obtained in the reaction unit 411 is recovered by the product storage unit 413.

As describe above, in accordance with the high-speed particle generating method of the present invention, the displacement mechanism 250 adjusts the setting positions of the components such that the positions of the emitting point P2 of the reference light L2, the condensing point P1 of the pulsed laser beam L1, and the high-speed particle generating target 400 surface each are conformed. Accordingly, the wave front of the pulsed laser beam L1 is compensated to be conformed with the reference wave front at the condensing point P1 on the high-speed particle generating target 400 surface based on the wave front (reference wave front) of the reference light L2. Thus, the pulsed laser beam L1 is condensed at a micro-spot (approximately 10 μm in diameter) on the high-speed particle generating target 400 surface, thereby obtaining a high-converging intensity (approximately $10^{18}$ W/cm$^2$). Therefore, it becomes possible to generate high-speed particles from the high-speed particle generating target 400.

Second Embodiment

Figure 7:
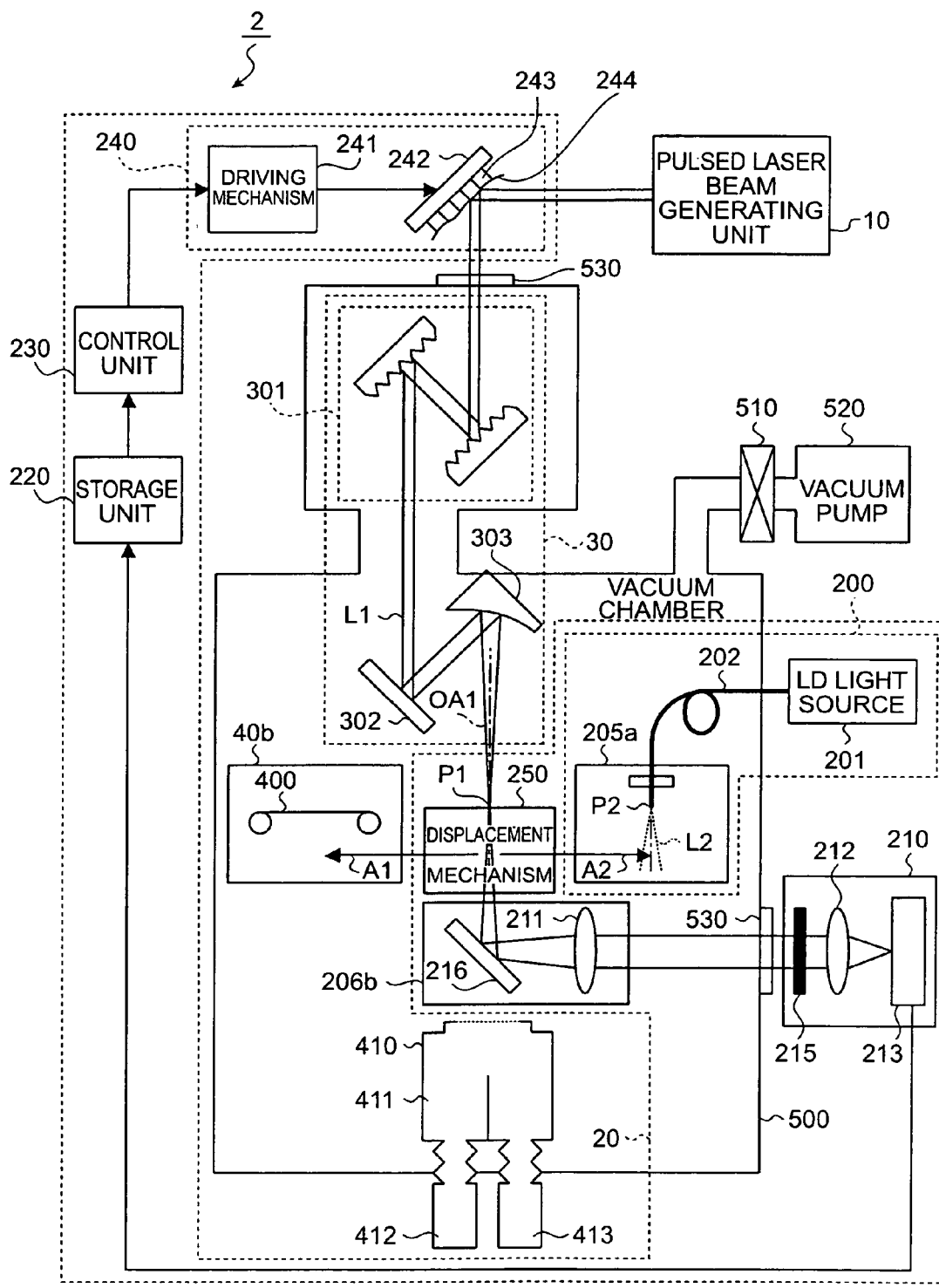
FIG. 7 is a view showing a construction of a second embodiment of the high-speed particle generating apparatus according to the present invention.

A second embodiment of the high-speed particle generating apparatus according to the present invention will next be explained with reference to FIG. 7. Note that in FIG. 7 the same symbols are denoted for the components identical or equal to those of the first embodiment.

The second embodiment is different from the aforementioned first embodiment in the structures of a collimator unit 206b and a target unit 40b, and the arrangements of a wave front measuring unit 210 and a reaction unit 410.

It is a difference from the first embodiment in that the collimator unit 206b has a mirror reflector 216 in addition to a collimator lens 211, and also the target unit 40b has only a high-speed particle generating target 400 without an isotope generating unit 410. Further, a wave front detecting unit 210 is arranged in the direction (right side in the drawing) such that a reference light L2 or pulsed laser beam L1 is reflected by the mirror reflector 216 with respect to the collimator unit 206b, while the reaction unit 410 is fixed and arranged in the direct advance direction (lower side in the drawing) of the pulsed laser beam L1 passing through the condensing point P1. At these points, the second embodiment is different from the first embodiment.

In accordance with the high-speed particle generating apparatus 2 of the second embodiment, when the respective wave fronts of the reference light L2 and pulsed laser beam L1 are measured, the reference light L2 and pulsed laser beam L1 incident on the collimator unit 206b arranged on the optical path each are reflected in the direction of the wave front measuring unit 210 by the mirror reflector 216. Then, the reference light L2 and pulsed laser beam L1 reflected by the mirror reflector 216 each are incident on the wave front measuring unit 210, and then the wave front is measured by the wave front sensor 213.

Next, when high-speed particles are generated, the displacement mechanism 250 displaces the collimator unit 206b in the direction of arrow A2; instead, the target unit 40b including only the high-speed generating target 400 is arranged on the optical path of the pulsed laser beam L1. Then, the condensed pulsed laser beam L1 is irradiated to the high-speed particle generating target 400, thereby generating high-speed particles from the high-speed particle generating target 400.

In this case, since it is required for the reaction unit 410 disposed in a vacuum chamber 500 to have a structure capable of enduring a pressure difference between an extremely lower pressure in vacuum and an atmospheric pressure, the weight of the unit 410 is very heavy. Accordingly, the displacement mechanism will be also given on a large scale for displacement of the reaction unit 410.

However, in accordance with the high-speed particle generating apparatus 2 of the second embodiment, since the aforementioned construction allows to fix and arrange the reaction unit 410, the displacement mechanism 250 having a simple structure is applicable thereto.

Third Embodiment

Figure 8:
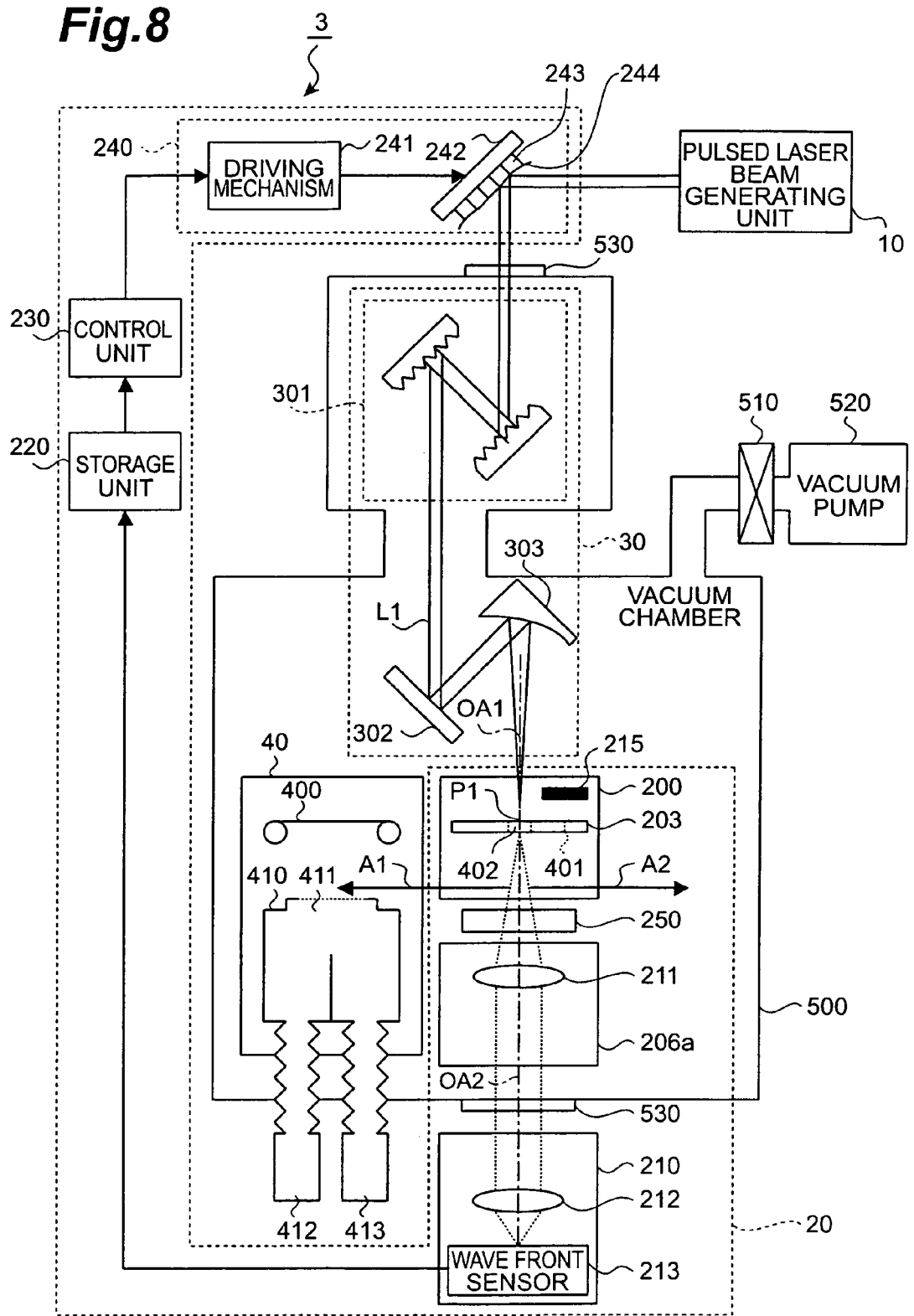
FIG. 8 is a view showing a construction of a third embodiment of the high-speed particle generating apparatus according to the present invention.
Figure 9:
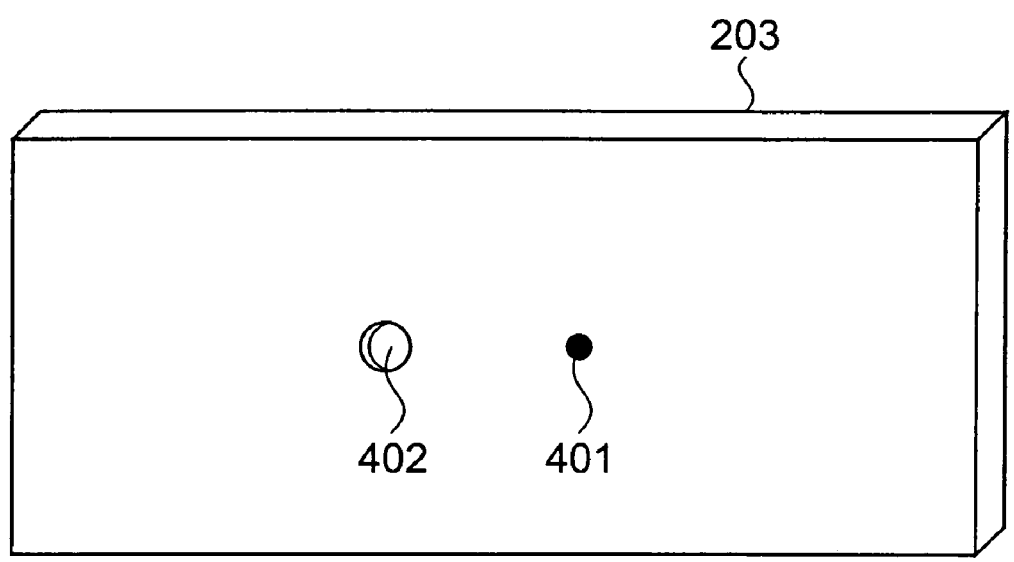
FIG. 9 is a view showing a construction of a reference light generating unit applied to the high-speed particle generating apparatus according to the present invention.

A third embodiment of the high-speed particle generating apparatus according to the present invention will next be explained with reference to FIGS. 8–9.

The third embodiment is different from the aforementioned first embodiment in that a reference light generating unit (reference light generating means) 203 having a pinhole 401 and an opening 402 is applied instead of the LD light source 201.

The reference light generating unit 203 generates a reference light L2 by entering a sufficiently intensity lowered pulsed laser beam L1 in a pinhole 401. This is based on using as a reference wave front an ideal spherical wave generated by diffraction when the laser beam passes through the micro-pinhole 401.

In accordance with the high-speed particle generating apparatus 3 of the third embodiment, the reference wave front is measured by use of the reference light L2 generated by entering the sufficiently intensity lowered pulsed laser beam L1 in the pinhole 401. Secondly, a displacement mechanism 250 displaces the reference wave front generating unit 203 in the direction of arrow A2, and thereby the opening 402 is disposed on the optical axis OA1 of the pulsed laser beam L1 to measure the wave front of the pulsed laser beam L1.

When high-speed particles are generated, the displacement mechanism 250 displaces the reference light generating unit 203 in the direction of arrow A2. Instead, a target unit 40 is disposed on the optical path of the pulsed laser beam L1. Then, the condensed pulsed laser beam L1 is irradiated to a high-speed particle generating target 400, thereby generating high-speed particles from the high-speed particle generating target 400.

As described above, according to the high-speed particle generating apparatus 3 according to the third embodiment, the reference wave front generating unit 203 having the pinhole 401 is applied thereto, thereby obtaining the reference light L2 easily.

Fourth Embodiment

Figure 10:
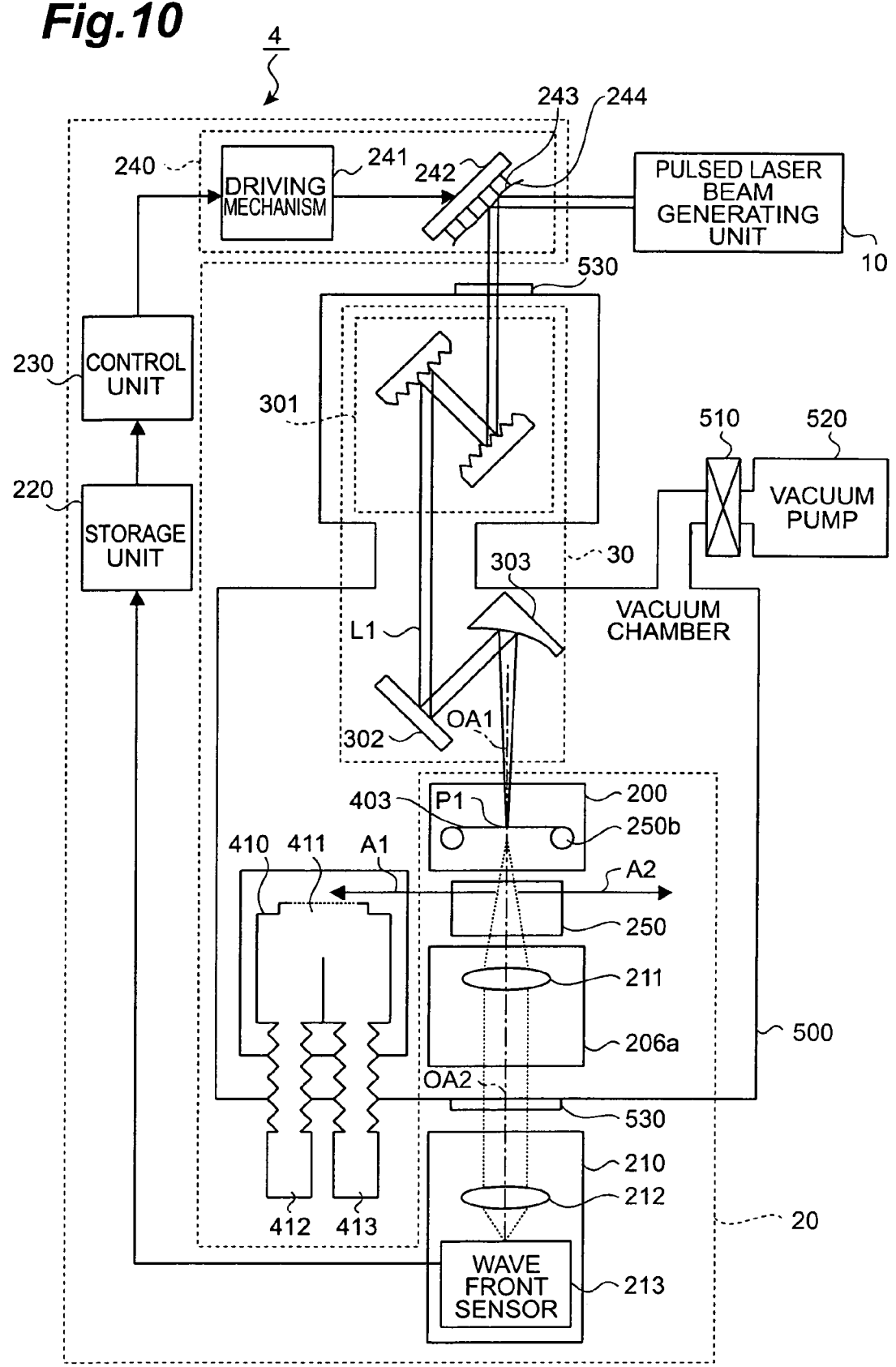
FIG. 10 is a view showing a construction of a fourth embodiment of the high-speed particle generating apparatus according to the present invention.

A fourth embodiment of the high-speed particle generating apparatus according to the present invention will next be explained with reference to FIGS. 10–11.

There is a difference from the aforementioned third embodiment in that a pinhole 401 and an opening 402 are formed in a high-speed particle generating target film 403 (including a high-speed particle generating target 400), and that a wind-up displacement mechanism 250b is applied for the displacement of the pinhole 401 and opening 402 instead of the reciprocating parallel motion-type displacement mechanism 250.

Figure 11:
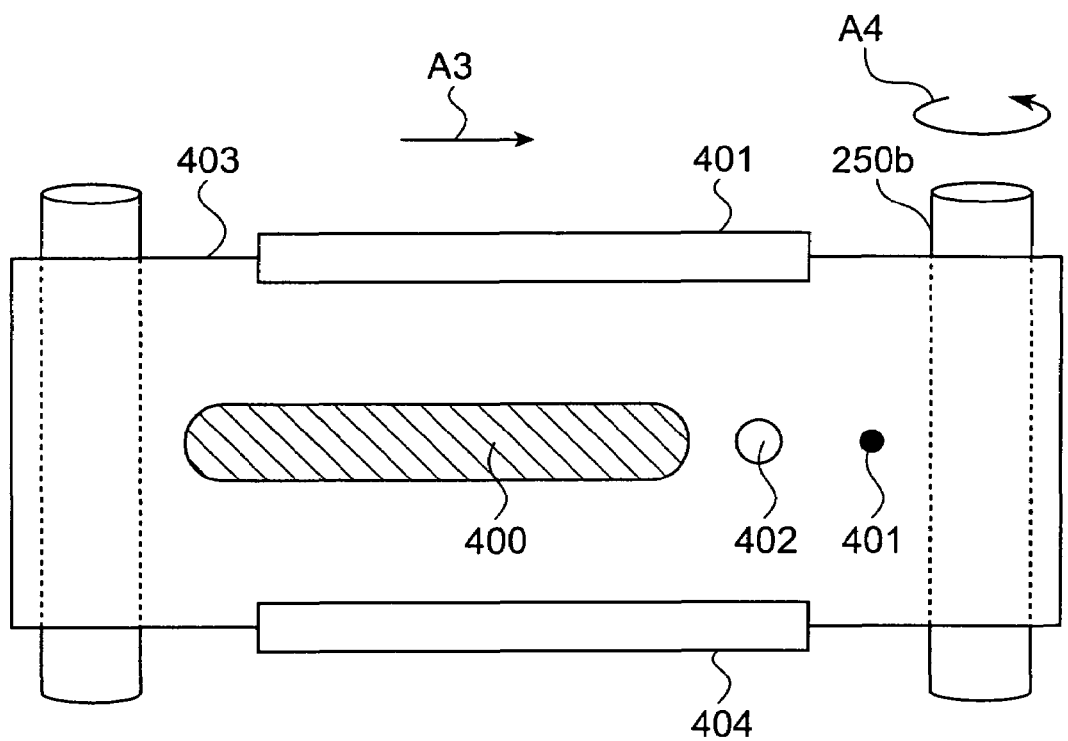
FIG. 11 is a view showing a high-speed particle generating target applied to the high-speed particle generating apparatus according to the fourth embodiment shown in FIG. 10.

As shown in FIG. 11, a tape-shaped porous film having a halogen-containing organic compound, for example, polytetrafluoroethylene and the like as a main component is suitable for the high-speed particle generating target film 403. Then, an organic compound, for instance, deuterated polystyrene and so on is impregnated at the central portion of the tape-shaped porous film along the longitudinal direction, thereby forming the stripe-shaped high-speed particle generating target 400. Further, the opening 402 for passing a pulsed laser beam L1 on the same straight line as that of the high-speed particle generating target 400 and the pinhole 401 for generating a reference wave front are formed in the high-speed particle generating target film 403.

The high-speed particle generating target 400 is held on a predetermined plane (a plane orthogonal to the optical axis OA1 in the fourth embodiment) by means of a guide unit 404 (corresponding to a target unit). On the other hand, when the cylindrical displacement mechanism 250b rolls up the high-speed particle generating target film 403 when it is rotated in the direction of arrow A4 by means of a driving mechanism. In this way, the high-speed particle generating target 400, pinhole 401 and opening 402 are displaced in the direction of arrow A3 (in the longitudinal direction of the high-speed particle generating target 400).

In accordance with the high-speed particle generating apparatus 4 of the fourth embodiment, the wave front of the reference light L2 is measured in a state where the pinhole 401 is arranged on the optical axis OA1 of the pulsed laser beam L1 by the displacement mechanism 250b, while the wave front of the reference light L1 is measured in a state where the opening 402 is arranged on the optical axis OA1 of the pulsed laser beam L1 by the displacement mechanism 250b. Then, the high-speed particle generating target 400 is arranged on the optical axis OA1 of the pulsed laser beam L1 by the displacement mechanism 250b, and high-speed particles will be generated from the high-speed particle generating target 400.

When the pulsed laser beam L1 is irradiated to the high-speed particle generating target 400, a hole is opened at that irradiated area, which cannot be reused any longer. However, when the high-speed particle generating target 400 is rolled up by the displacement mechanism 250b, and the high-speed particle generating target 400 is displaced in the direction of arrow A3, a new target surface can be set.

In accordance with the high-speed particle generating apparatus 4 of the fourth embodiment, the respective wave fronts of the pulsed laser beam L1 and reference light L2 are measured and further the wave front of the pulsed laser beam L1 is compensated by use of the pinhole 40 and opening 402 that are formed on the same plane as that of the high-speed particle generating target 400. Therefore, it becomes possible to carry out the compensation of the wave front of the pulsed laser beam L1 with high positional precision.

Five Embodiment

Figure 12:
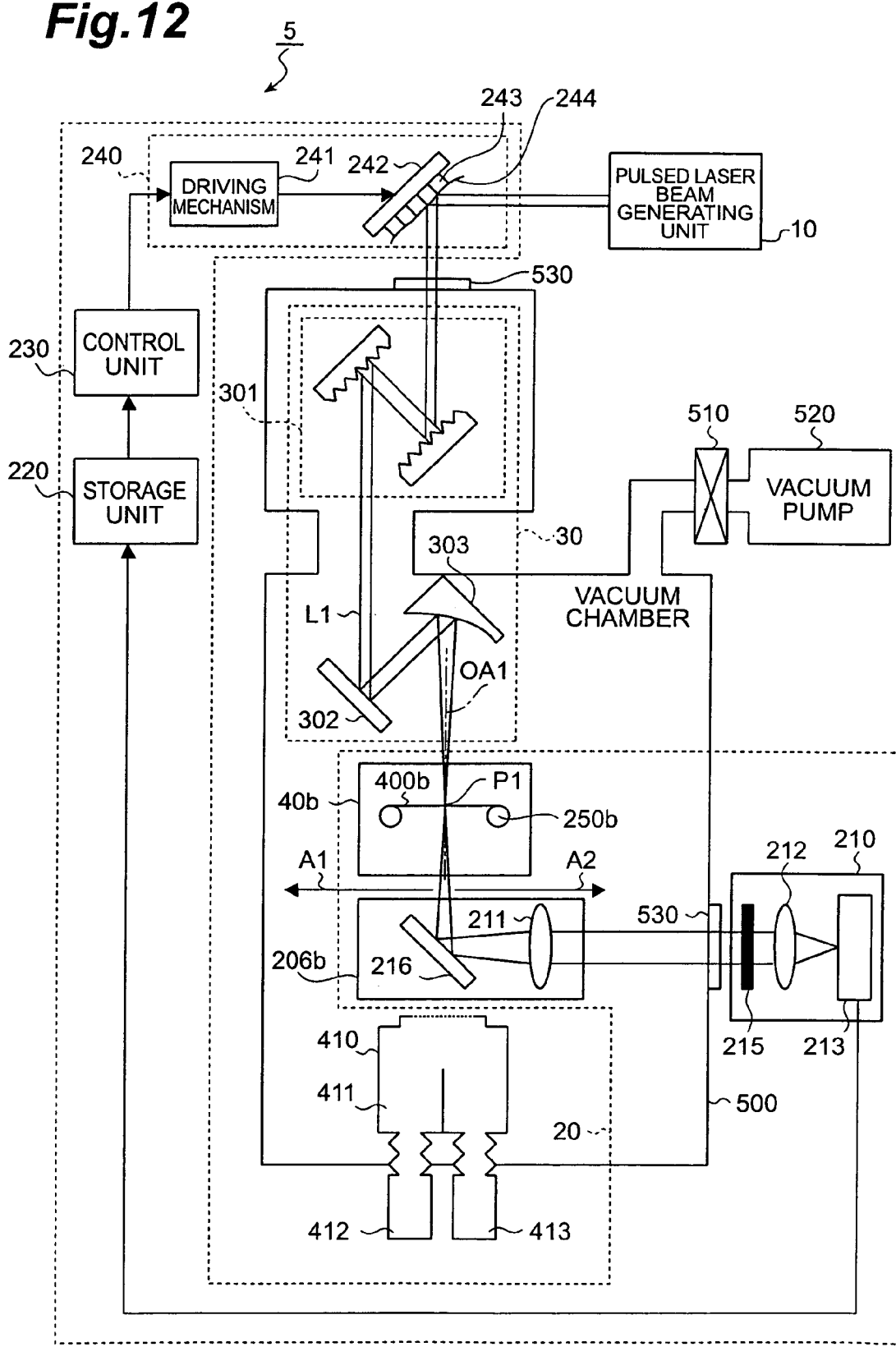
FIG. 12 is a view showing a construction of a fifth embodiment of the high-speed particle generating apparatus according to the present invention.

A fifth embodiment of the high-speed particle generating target according to the present invention will next be explained with reference to FIG. 12.

The fifth embodiment is different from the aforementioned second embodiment in that instead of the LD light source 201 a high-speed particle generating target film 403 is applied, which is formed with a pinhole 401 and an opening 402 on the same straight line as that of a stripe-shaped target area 400.

In such a construction, it becomes to fix and arrange a reaction unit 410, and the displacement mechanism 250 may be unnecessary, thereby performing a simplified construction. In addition, it becomes possible to carry out the compensation of the wave front of the pulsed laser beam L1 with high positional precision.

In addition, the following method is also effective in order to generate high-speed particles efficiently from a high-speed particle generating target. Namely, the shape of form of a reflecting surface 244 of a deformable mirror 242, the wave front of the pulsed laser beam L1 at that time is stored, and the amount of the product obtained in the reaction unit 410 is measured. Then, when a condition of the wave front such that more product may be yielded is searched, an optimum condition of the wave front of the pulsed laser beam L1 can be obtained. Then, the optimum wave front is stored as a reference wave front, and a wave front compensation is conducted to match the wave front of the pulsed laser beam with the reference wave front. In such a way, high-speed particles can be generated from the high-speed particle generating target efficiently.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

INDUSTRIAL APPLICABILITY

As descried above, in accordance with the present invention, a high-speed particle generating method and a high-speed particle generating apparatus can be obtained, which is capable of generating high-speed particles from a high-speed particle generating target when a pulsed laser beam is condensed at a micro-spot on the surface of the high-speed particle generating target.

The invention claimed is:

1. A high-speed particle generating method which condenses a pulsed laser beam generated from a pulsed laser beam generator at a predetermined condensing point through an irradiation optical system, and irradiates the pulsed laser beam to a high-speed particle generating target that is set at the predetermined condensing point, thereby generating high-speed particles from the high-speed particle generating target, said method further comprising the steps of:
   a first step of generating a reference light from the predetermined condensing point, measuring the wave front of the reference light by using a wave front measuring device, and storing the measured wave front as a reference wave front;
   a second step of measuring the wave front of the pulsed laser beam generated from said pulsed laser beam generator and passing through the predetermined condensing point by using said wave front measuring device; and
   a third step of compensating the wave front of the pulsed laser beam from said pulsed laser beam generator based on the reference wave front.

2. A high-speed particle generator comprising:
   a target unit for holding at a predetermined position a high-speed particle generating target that generates high-speed particles when laser plasma is generated due to irradiation of a pulsed laser beam;
   a pulsed laser beam generator for generating the pulsed laser beam;
   a wave front compensating unit for compensating the wave front of said pulsed laser beam; and
   an irradiation optical system for condensing at a predetermined condensing point the pulsed laser beam of which the wave front is compensated by said wave front compensating unit,
   wherein said wave front compensating unit comprises:
   a deformable optical system such that an optical operation unit of an optical element for reflecting or deflecting the pulsed laser beam is deformably constituted;
   a reference light source for generating a reference light from the predetermined condensing point;
   a wave front measuring device for measuring the wave front of the reference light and the wave front of the pulsed laser beam passing through said predetermined condensing point, respectively;
   a storing unit for storing as a reference wave front the wave front of said reference light measured by said wave front measuring device;
   a deformable optical system control unit for compensating the wave front of the pulsed laser beam in such a manner that said optical operation unit is deformed based on the wave front of the pulsed laser beam and the reference wave front measured by using said wave front measuring device;
   a displacement mechanism for displacing said reference light source so that the emission position of the reference light is conformed at the predetermined condensing point, or displacing said target unit so that the high-speed particle generating target is conformed with a plane including the predetermined condensing point.

3. A high-speed particle generator comprising:
   a target unit for holding at a predetermined position a high-speed particle generating target that generates high-speed particles when laser plasma is generated due to irradiation of a pulsed laser beam;
   a pulsed laser beam generator for generating the pulsed laser beam;
   a wave front compensating system for compensating the wave front of the pulsed laser beam; and
   an irradiation optical system for condensing at a predetermined condensing point the pulsed laser beam of which the wave front is compensated by using said wave front compensating system,
   wherein said wave front compensating system comprises:
   a deformable optical system such that an optical operation unit of an optical element for reflecting or deflecting the pulsed laser beam is deformably constituted;
   a reference light generating unit having a pinhole for generating a reference light from the predetermined condensing point by passing through the pulsed laser beam;
   a wave front measuring device for measuring the respective wave fronts of the reference light and the pulsed laser beam passing through the predetermined condensing point, respectively;
   a storing unit for storing as a reference wave front the wave front of the reference light measured by using said wave front measuring device;
   a deformable optical system control unit for compensating the wave front of the pulsed laser beam in such a manner that said optical operation unit is deformed based on both of the wave front of the pulsed laser beam measured by using said wave front measuring device and the reference wave front;
   a displacement mechanism for displacing said reference light generating unit and said target unit holding the high-speed particle generating target, respectively, on a plane including the predetermined condensing point.

4. A high-speed particle generating apparatus according to claim 3, wherein the high-speed particle generating target is formed on the surface of a membrane target member,
   wherein an opening for passing through the pulsed laser beam and a pinhole are formed in said target member, and
   wherein the wave front of the pulsed laser beam having passed through said opening is measured by using said wave front measuring device.

* * * * *